United States Patent [19]

Wendling

[11] 4,249,011
[45] Feb. 3, 1981

[54] POLY(ETHYLENICALLY UNSATURATED ALKOXY) HETEROCYCLIC COMPOUNDS

[75] Inventor: Larry A. Wendling, St. Paul, Minn.

[73] Assignee: Minnesota Mining and Manufacturing Company, St. Paul, MN

[21] Appl. No.: 51,876

[22] Filed: Jun. 25, 1979

[51] Int. Cl.³ ............... C07D 233/72; C07D 233/96
[52] U.S. Cl. .................. 548/312; 548/307; 544/221; 544/222; 544/301; 544/302; 544/311; 544/314; 544/312
[58] Field of Search ............... 548/307, 312

[56] References Cited

U.S. PATENT DOCUMENTS

| | | |
|---|---|---|
| 3,808,226 | 4/1974 | Habermeier et al. ............ 548/312 |
| 3,821,098 | 6/1974 | Garratt et al. ............ 204/159.22 |
| 3,847,769 | 11/1974 | Garratt et al. ............ 204/159.22 |
| 3,852,302 | 12/1974 | Habermeier et al. ............ 548/312 |
| 4,071,477 | 1/1978 | Seltzer et al. ............ 548/309 |

Primary Examiner—Henry R. Jiles
Assistant Examiner—Natalia Harkaway
Attorney, Agent, or Firm—Cruzan Alexander; Donald M. Sell; Mark A. Litman

[57] ABSTRACT

Ethylenically unsaturated crosslinking agents and polymerizable monomers are disclosed. These agents contain a heterocyclic nucleus and are capable of forming oxygen insensitive, radiation curable systems.

15 Claims, No Drawings

POLY(ETHYLENICALLY UNSATURATED ALKOXY) HETEROCYCLIC COMPOUNDS

FIELD OF THE INVENTION

The present invention relates to novel ethylenically unsaturated crosslinking agents and to radiation curable compositions containing these agents. The invention particularly relates to ethylenically unsaturated heterocyclic crosslinking agents, to radiation curable oxygen insensitive compositions containing such agents, and to alcohol or aqueous alcohol developable imaging layers containing such compositions.

DESCRIPTION OF THE PRIOR ART

The generation of three dimensional bonding or crosslinking in a composition or coating to reduce the solubility and improve the chemical resistance of a cured product is well known. This is usually effected by the addition of a crosslinking agent to an otherwise two dimensionally polymerizable composition from which the cured product is made. Crosslinking has been produced in products from ethylenically unsaturated compositions such as acrylic compositions (e.g. a methyl methacrylate composition) by incorporation of from about 1 to about 10 percent by weight of a polyacrylic substituted compound as a crosslinking agent. It is well known that such acrylic compositions generally must be polymerized in an inert atmosphere, e.g., a nitrogen atmosphere. Otherwise, the oxygen present in air will retard or even prevent polymerization of the acrylic composition so that desired levels of polymerization cannot be achieved. At best, only a tacky, incompletely polymerized resin or a weak, low molecular weight polyacrylate resin can be obtained.

Curable, oxygen insensitive acrylic compositions are described in U.S. Pat. Nos. 3,844,916, 3,914,165 and 3,925,349. These references teach that oxygen inhibition can be avoided by incorporation of a Michael adduct of a polyacrylate and an amine having at least one amino hydrogen into acrylic compositions. The use of such an adduct in acrylic photopolymerizable compositions requires the use of a relatively high concentration of polymerization photoinitiator (3% by weight is disclosed at Col. 3, lines 50–51 of U.S. Pat. No. 3,925,349). Although such compositions are useful for coatings and inks that can be cured in the presence of oxygen, these compositions are not satisfactory for coatings that are transparent and where discoloration is undesirable since the use of large amounts of photoinitiator leads to yellowing of the cured coating.

Acrylic compositions, containing 0.5 to 10 percent triphenyl phosphine, that can be cured rapidly in an atmosphere containing 300 to 1000 ppm of oxygen are disclosed in U.S. Pat. No. 4,113,893. Since the provision of atmosphere containing oxygen in any concentration less than that found in air requires use of special equipment, the use of phosphines to obtain rapid curing is also unsatisfactory for many commercial processes.

U.S. Pat. No. 3,968,305 describes acrylic compositions comprising an aliphatic compound having three or more methacryloxy groups that can be polymerized to a crosslinked mar resistant coating. U.S. Pat. No. 4,014,771 teaches that by the addition of (1) 30 to 95 percent of the adduct of methacrylic acid and (2) either a polyglycidyl ether of an aromatic polyhydric compound or a polyglycidyl ester of an aromatic or aliphatic polycarboxylic acid to a polymethacryloxy compound such as that described in U.S. Pat. No. 3,968,305, there is obtained a composition which evidently can be polymerized without the necessity of excluding air during the polymerization.

Protective coatings produced by irradiation in the absence of air of the adduct of methacrylic acid to N-glycidylheterocyclic compounds are disclosed in U.S. Pat. Nos. 3,808,226 and 3,847,769. Polymerization of the dimethacrylic ester of N-oxyalkylated-heterocyclic compounds is disclosed in U.S. Pat. Nos. 3,821,098 and 3,852,302.

The compounds of U.S. Pat. No. 3,808,226 bear a similarity in structure to the compounds of the present application. The route of synthesis shown for those compounds can not produce the compounds of the present invention nor could the route of synthesis used in the present invention produce the compounds of that patent.

SUMMARY OF THE INVENTION

In accordance with the invention, there are provided novel ethylenically unsaturated crosslinking agents comprising poly(ethylenically unsaturated alkoxyalkyl)heterocyclic compounds and a process for their preparation. The crosslinking agents of the invention have the general formula:

$$A^1-Z-A^2 \qquad \text{I}$$

in which $A^1$ and $A^2$ independently are alkoxyalkyl groups having terminal ethylenic unsaturation and having the general formula:

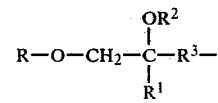

in which R—O— is a monovalent residue (formed by removal of the active hydrogen from an —OH group) of an aliphatic terminally unsaturated primary alcohol, ROH, R having the formula:

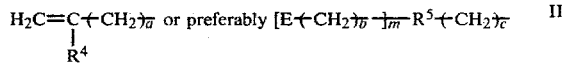

wherein:
E is

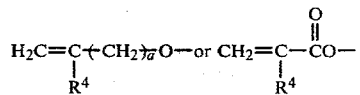

a and c are independently an integer of 1 to 6,
b is zero or an integer of 1 to 6,
$R^1$ and $R^4$ are independently hydrogen or methyl,
$R^5$ is an aliphatic group having 1 to 15 carbon atoms (preferably alkylene of up to 15 carbon atoms) and optionally one or two catenary (i.e., backbone) oxygen atoms, or

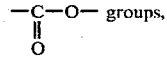

a valence of m+1, and
m is an integer of 1 to 5,
R² is preferably hydrogen but can be

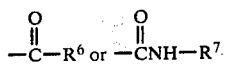

wherein R⁶ is preferably alkenyl but can be alkyl (each preferably having 2 to 5 carbon atoms) and can be substituted by a phenyl or carboxyl group and R⁷ is an aliphatic group (of up to eight carbon atoms, e.g., alkyl) or aromatic group (preferably having up to 8 carbon atoms and more preferably a phenyl group) and R⁷ is most preferably an acryloyloxyalkyl or a methacryloyloxyalkyl group, R³ is an alkylene group having 1 to 6 carbon atoms and optionally one catenary oxygen atom; and Z is a heterocyclic group of the formula:

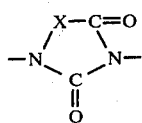

wherein:

X is a divalent group which is required to complete a 5- or 6-membered heterocyclic ring, preferably X is

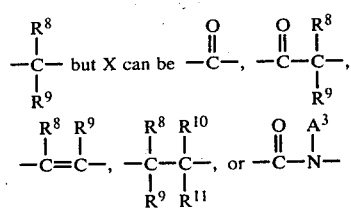

wherein R⁸, R⁹, R¹⁰, and R¹¹ are independently hydrogen or lower alkyl (of 1 to 4 carbon atoms), cycloalkyl (of 3 to 6 carbon atoms) or phenyl group (of 6 to 12 carbon atoms) and A³ is an alkoxyalkyl group as defined above for A¹ and A².

The preferred compounds of Formula I are those wherein E is

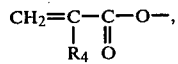

m is 2 to 5, and X is

These compounds are preferred because they provide not only a high crosslink density, resulting in improved solvent and abrasion resistance but also excellent adhesion and flexibility. Furthermore, these compounds are water/alcohol soluble and are photocurable to tack free surfaces in the presence of atmosphere oxygen.

This invention further includes energy crosslinkable compositions particularly to photocurable compositions comprising the poly(ethylenically unsaturated alkoxyalkyl)heterocyclic compounds of the present invention and a polymerization catalyst which liberates free radicals on application of energy.

DETAILED DESCRIPTION OF THE INVENTION

The compounds of the invention can be prepared by the Lewis acid catalyzed addition of n moles of an ethylenically unsaturated primary alcohol to an epoxy-substituted heterocycle in accordance with the equation:

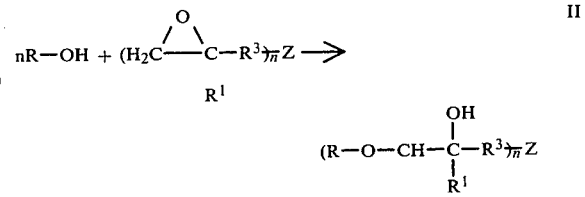

wherein R, R¹, R³, and Z are as defined for the compounds of Formula I, and n is 2 or 3.

Particularly, the (polyacrylyloxy)alkoxypropylheterocyclic compounds of the invention are 5- or 6-membered ring heterocyclic compounds having preferably two (but may have three) nitrogen and preferably two (but may have three) carbonyl groups, viz.

in the ring. At least one but preferably all of the ring nitrogens are substituted by a (polyacryloyloxy)alkoxypropyl group (e.g., Formula II). The substituted heterocyclic compounds can be prepared (as shown above) by the Lewis acid catalyzed addition to a heterocyclic compound, as defined, that has one, two or three (where present) of its ring nitrogens substituted by a glycidyl group (e.g., a 2,3-epoxypropyl group) of one, two or three equivalents of a hydroxy compound that is the product of esterification of m hydroxyl groups of a polyol having (m+1) hydroxyl groups with acrylic or methacrylic acid in accordance with the equation:

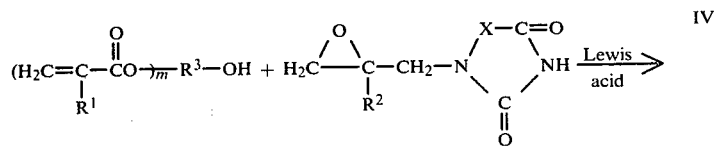

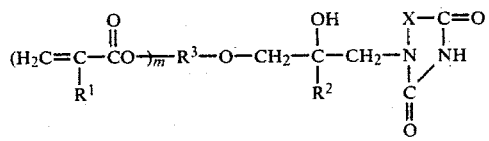

wherein $R^1$, $R^2$, m, $R^3$ and X are defined above.

The above equation illustrates the preparation where only one of the ring nitrogens has been substituted by the glycidyl group. Where two or three of the ring nitrogens have been substituted by glycidyl (as is most preferable), two or three equivalents of hydroxy compound can be added. The addition of the hydroxy compound to the glycidyl groups of the heterocyclic compound can be done in one step or in a sequence of steps in which first one and then a second and then a third glycidyl group is reacted. It is not necessary that the same hydroxy compound be used in each of the steps. Where two or more different hydroxy compounds are used, unsymmetrical compounds are obtained, that is, $A^1$ and $A^2$ (and $A^3$ if three nitrogens on the ring) of Formula I are different. Mixtures of hydroxy compounds can also be used. It is to be expected, however, when two or more hydroxy compounds are used, whether in a sequence of steps or in a one-step mixture, the product obtained will be a mixture of (polyacryloyloxy)alkoxypropylheterocyclic compounds. All, however, are useful in the present invention, particularly when at least about 30% by weight of the polymerizable coating composition is a heterocyclic compound having at least two glycidyl groups reacted with hydroxy compounds in which m in Formula I is at least three; that is, the hydroxy compound to be reacted with the glycidyl group of the heterocyclic compound is preferably a tri- or higher acryloyloxy or methacryloyloxy-hydroxy compound.

The polyglycidyl heterocyclic intermediates useful in the preparation of any and all of the compounds of the present invention are disclosed in U.S. Pat. Nos. 3,808,226 and 4,071,477. Preferably, the reaction is performed in solution. However, it also can be performed in the absence of solvent. Generally, a solution of an epoxy-substituted heterocycle can be added incrementally (over a period of time ranging from a few minutes to several hours) to a mixture of (1) an ethylenically unsaturated primary alcohol (or mixtures of ethylenically unsaturated primary alcohols), (2) an inhibitor for thermal polymerization, and (3) a Lewis acid while maintaining the temperature of the mixture at 50° to 120° C., preferably about 80° to 100° C., until the disappearance of the epoxy group, as indicated by chemical titration or nuclear magnetic resonance spectrometric analysis. Heating the mixture for from 2 to 40 hours usually suffices to complete the reaction, after which volatiles are removed by vacuum distillation.

The compounds of Formula II can then be acylated by reaction with an acylating agent, preferably an acyl halide, an acyl anhydride, or an isocyanate that contains polymerizable ethylenically unsaturated groups. Preferred acylated compounds have the Formula:

$$
\begin{array}{cc}
\text{O} \\
\| \\
\text{OCR}^6 \\
| \\
(R\text{--}O\text{--}CH_2\text{--}C\text{--}R^3)_{n}Z \\
| \\
R^1
\end{array}
\quad \text{III}
$$

or $$
\begin{array}{cc}
\text{O} \\
\| \\
\text{OC--NH--}R^7 \\
| \\
(R\text{--}O\text{--}CH_2\text{--}C\text{--}R^3)_{n}Z \\
| \\
R^1
\end{array}
\quad \text{IV}
$$

wherein R, $R^1$, $R^3$, $R^6$, $R^7$, z, m and n are as defined for Formula I.

Exemplary acylating agents include acid chlorides such as acetyl chloride, propionyl chloride, valeryl chloride, dodecanyl chloride, acrylolyl chloride, methacryloyl chloride, alpha-chloroacryloyl chloride, crotyl chloride, benzoyl chloride, phenylacetyl chloride, 2,4-dichlorophenylacetyl chloride; and the corresponding carboxylic acids and anhydrides; other anhydrides include the anhydrides of dicarboxylic acids such as maleic anhydride, succinic anhydride, methylenesuccinic anhydride, phthalic anhydride, and 3-chlorophthalic anhydride; and organic isocyanates such as methyl isocyanate, ethyl isocyanate, n-butyl isocyanate, phenyl isocyanate, 4-t-butyl isocyanate, acryloyloxyethyl isocyanate, methacryloyloxyethyl isocyanate, 4-methacryloyloxybutyl isocyanate, 4-acryloylphenyl isocyanate and 4-vinylphenyl isocyanate.

The compounds of Formulas III and IV of the invention are prepared by addition of a suitable acylating agent to the compound II, e.g. an organic acid anhydride or halide or an organic isocyanate.

Suitable ethylenically unsaturated primary alcohols for use in the preparation of the compounds of the invention are the hydroxylalkyl acrylates having the formula:

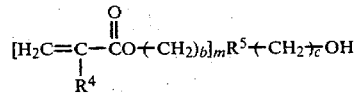

in which $R^4$, $R^5$, m and c are the same as defined for compounds of Formula I. Included among suitable hydroxyalkyl acrylates are the monoacrylate and monomethacrylate esters of aliphatic diols such as ethyleneglycol, propyleneglycol, butyleneglycol, hexamethyleneglycol, diethyleneglycol, and dimethylolcyclohexane; the diacrylates and dimethacrylates of aliphatic triols such as trimethylolmethane, 1,1,1-trimethylolpropane, 1,2,3-trimethylolpropane; the triacrylates and trimethacrylates of aliphatic tetrols such as pentaerythritol, 1,1,2,2-tetramethyloiethane and 1,1,3,3-tetramethylopropane; the tetraacrylates and tetramethacrylates of polyols such as dipentaerythritol and 1,1,1,2,2-pentamethylolethane; and the pentaacrylates and pentamethacrylates of polyols such as tripentaerythritol and hexamethylolethane.

Other suitable ethylenically unsaturated primary alcohols for use in the preparation of the compounds of the invention are the hydroxyalkenes having the formula:

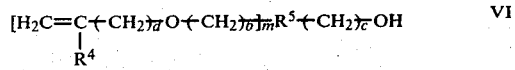   VI in which $R^4$, $R^5$, m, d, b, and c are the same as defined for compounds of Formula I. Included among suitable hydroxyalkenes are allyl alcohol, methallyl alcohol, allyloxyethyl alcohol, 2-allyloxymethylpropanol (from dimethylolethane), and 2,2-di(allyloxymethyl)butanol (from trimethylolpropane).

Polymerization initiators suitable for use in the crosslinkable compositions of the invention are compounds which liberate or generate a free-radical on addition of energy. Such initiators include peroxy, azo, and redox systems each of which are well known and are described frequently in polymerization art, e.g. Chapter II of *Photochemistry*, by Calvert and Pitts, John Wiley & Sons (1966). Included among free-radical initiators are the conventional heat activated catalysts such as organic peroxides and organic hydroperoxides; examples are benzoyl peroxide, tertiary-butyl perbenzoate, cumene hydroperoxide, azobis(isobutyronitrile) and the like. The preferred catalysts are photopolymerization initiators which facilitate polymerization when the composition is irradiated. Included among such initiators are acyloin and derivatives thereof, such as benzoin, benzoin methyl ether, benzoin ethyl ether, benzoin isopropyl ether, benzoin isobutyl ether, and α-methylbenzoin; diketones such as benzil and diacetyl, etc.; organic sulfides such as diphenyl monosulfide, diphenyl disulfide, decyl phenyl sulfide, and tetramethylthiuram monosulfide; S-acyl dithiocarbamates, such as S-benzoyl-N,N-dimethyldithiocarbamate; phenones such as acetophenone, α,α,α-tribromacetophenone, α,α-diethoxyacetophenone, 2,2-dimethoxy-2-phenylacetophenone, o-nitro-α,α,α-tribromacetophenone benzophenone, and p,p'-tetramethyldiaminobenzophenone; aromatic iodonium and aromatic sulfonium salts; sulfonyl halides such as p-toluenesulfonyl chloride, 1-naphthalenesulfonyl chloride, 2-naphthalenesulfonyl chloride, 1-3benzenedisulfonyl chloride, 2,4-dinitrobenzenesulfonyl bromide and p-acetamidobenzenesulfonyl chloride. Normally the initiator is used in amounts ranging from about 0.01 to 5% by weight of the total polymerizable composition. When the quantity is less than 0.01% by weight, the polymerization rate becomes extremely low. If the initiator is used in excess of 5% by weight, no correspondingly improved effect can be expected. Thus, addition of such greater quantity is economically unjustified. Preferably, about 0.25 to 1.0% of initiator is used in the polymerizable compositions.

The crosslinkable compositions of the invention are preferably diluted with an ethylenically unsaturated monomer. Suitable ethylenically unsaturated monomers include methyl methacrylate, ethyl acrylate, 2-ethylhexyl acrylate, cyclohexyl acrylate, styrene, 2-chlorostyrene, 2,4-dichlorostyrene, acrylic acid, acrylamide, acrylonitrile, t-butyl acrylate, methyl acrylate, butyl acrylate, 2-(N-butylcarbamyl)ethyl methacrylate and 2-(N-butylcarbamyl)ethyl methacrylate and 2-(N-ethylcarbamyl) ethyl methacrylate. Other diluting monomers that can be incorporated into the composition of the invention include 1,4-butylene dimethacrylate or acrylate, ethylene dimethacrylate, hexanediol diacrylate or dimethacrylate, glyceryl diacrylate or methacrylate, glyceryl triacrylate or trimethacrylate, pentaerythritol triacrylate or trimethacrylate, pentaerythritol tetraacrylate or tetramethacrylate, diallyl phthalate, dipentaerythritol pentaacrylate, neopentylglycol triacrylate and 1,3,5-tri(2-methacryloxyethyl)-s-triazine.

The crosslinkable composition can also contain a viscosity modifier or binder. Generally, up to about 50 percent by weight of a compatible polymer is used. Preferably, the polymer is an acrylic polymer such as poly(acrylic acid), a poly(methacrylic acid), poly(methyl methacrylate), poly(vinyl chloride), poly(vinyl acetate, poly(vinyl butyral) and the like. Other polymers include polyethers, polyesters, polylactones, polyamides, polyurethanes, cellulose derivatives, polysiloxanes and the like.

The compositions of the invention can also include a variety of addenda utilized for their known purpose, such as stabilizers, inhibitors, lubricants, flexibilizers, pigments, carbon black, dyes, reinforcing fillers such as finely divided silica, non-reinforcing fillers such as diatomaceous earth, metal oxides, asbestos, fiberglass, glass bubbles, talc, etc. Fillers can generally be used in proportions up to about 200 percent by weight of the curable components but preferably are used up to about 50 percent by weight. Where the polymerizing energy is radiation, it is desirable that the addenda be transparent to the radiation.

The compositions of the invention are prepared by simply mixing (under "safe light" conditions if the composition is to be sensitized to visible light) the polymerization catalyst and sensitizer (where used), the poly(ethylenically unsaturated alkoxyalkyl)heterocyclic compound, diluting monomers, binders and addenda. Inert solvents may be employed if desired when effecting this mixture. Examples of suitable solvents are methanol, ethanol, acetone, acetonitrile and includes any solvent which does not react with the components of the mixture.

Utility

The crosslinkable compositions of the invention can be used as adhesives, caulking and sealing compositions, casting and molding compositions, potting and encapsulating compositions, impregnating and coating compositions, etc., depending on the particular combination of components. Where the polymerization catalyst is a photoinitiator, the composition can be a composition for in situ curing because of this insensitivity to oxygen.

The photopolymerizable compositions are particularly suitable for applications in the field of protective coatings and graphic arts because of their superior abrasion-resistance and adhesion to many rigid, resilient and flexible substrates such as metals, plastics, rubber, glass, paper, wood, and ceramics; their excellent resistance to most solvents and chemicals; their excellent flexibility and weatherability; and their capability for forming high resolution images. Among such uses are water or water/alcohol developable resists for chemical milling, gravure images, offset plates, stencil making, screenless lithography, particulate binders as in microtaggants, relief printing plates, printed circuits, electron beam curing adhesives, radiation and protective coatings for glass, metal surfaces and the like. Priming layers may be used if desired, and in some cases may be necessary.

The photopolymerization of the compositions of the invention occurs on exposure of the compositions to any source of radiation emitting actinic radiation at a wavelength within the ultraviolet and visible spectral regions. Suitable sources of radiation include mercury, xenon, carbon arc and tungsten filament lamps, sunlight, etc. Exposures may be from less than about 1 second to 10 minutes or more depending upon the amounts of the particular polymerizable materials and photopolymerization catalyst being utilized and depending upon the radiation source, distance from the source, and the thickness of the coating to be cured. The compositions may also be polymerized by exposure to electron beam irradiation. Generally speaking, the dosage necessary is from less than 1 megarad to 100 megarad or more. One of the major advantages with using electron beam curing is that highly pigmented compositions can be effectively cured at a faster rate than by mere exposure to actinic radiation.

These and other features of the present invention will be shown in the following Examples.

EXAMPLE 1

Preparation of
1,3-Bis(3-[2,2,2-(triacryloyloxymethyl)ethoxy
2-hydroxypropyl]-5,5-dimethyl-2,4-imidizolidinedione

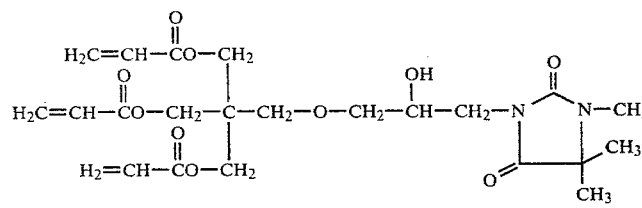 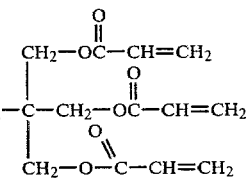

Compound A

Pentaerythritol triacrylate (44.3 g, 0.1 m, hydroxyl equivalent weight of 443), 0.025 g 4-methoxyphenol, and 0.4 g borontrifluoride etherate were charged into a 250 ml three-necked round bottom flask equipped with mechanical stirrer, pressure equalizing dropping funnel, reflux condenser, and a $CaSO_4$ drying tube. (It is to be noted that most commercially available pentaerythritol triacrylate is contaminated with acrylated impurities.). The reaction flask was heated to 60° C. and 13.8 g of 1,3-bis(2,3-epoxypropyl)-5,5-dimethyl-2,4-imidizolidinedione (0.1 m epoxide equivalency) in 5 ml chloroform was added dropwise over 45 minutes. After the addition, the reaction flask temperature was raised to 85° C. and stirred for 11.5 hours. After this time, titration of an aliquote for unreacted epoxide indicated that the reaction was greater than 99% complete. The chloroform was removed by vacuum distillation leaving as residue a viscous liquid that contains predominently compounds of the structure of Compound A. Photocurable impurities introduced with the pentaerythritol triacrylate can be removed by trituration with diethyl ether.

A mixture of the liquid and 2% by weight of the photopolymerization initiator 2,2-dimethoxy-2-phenylacetophenone was coated onto 12 μm polyester film and dried to provide a 2.5 μm layer. The layer was then cured in a UV Processor, Model No. CC 1202 N/A (manufactured by Radiation Polymer Co.) after one pass at 12 m/min. (40 feet/min.) under an 80 watts/cm (200 watts/inch) medium pressure mercury lamp. The cured layer exhibited 95–100% cross-hatch adhesion, 2–7% Taber Haze, 13–16% haze in the Gardner Falling Sand Abrader (i.e., tested according to ASTM Designation D1003-64(Procedure A)) and excellent resistance to abrasion by steel wool. The layer was unaffected by treatment with ethanol, acetone, ethyl acetate, toluene, hexane, aqueous sodium hydroxide and 10% aqueous hydrochloric acid.

EXAMPLES 2–3

Preparation of
1,3-Bis[3-(2-acryloyloxyethoxy)-2-hydroxypropyl]-5,5-dimethyl-2,4-imidizolidinedione

Compound B

Distilled hydroxyethyl acrylate (46.4 g, 0.4 m), 0.065 g 4-methoxyphenol, and 1.0 g borontrifluoride etherate were charged into a 250 ml three-necked round bottom flask equipped with mechanical stirrer, pressure equalizing dropping funnel, reflux condenser, and $CaSO_4$ drying tube. The reaction flask was heated to 60° C. and 55.2 g 1,3-bis(2,3-epoxypropyl)-5,5-dimethyl-2,4-imidizolidinedione in 10 ml chloroform was added dropwise over 30 minutes. The reaction flask temperature was raised to 75° C. for 11 hours. At this time titration of residual epoxide groups indicated that the reaction was 97% complete. The volatiles were removed by vacuum distillation leaving as residue a liquid.

A layer of the compound containing 2% of 2,2-dimethoxy-2-phenylacetophenone was prepared and cured as in Example 1. The cured layer had chemical resistance similar to that of the layer of Example 1.

The analogous dimethacryloyl derivative (Compound C) was prepared in a similar manner utilizing 2-hydroxyethyl methacrylate in place of 2-hydroxyethyl acrylate. Layers prepared and cured with Compound C in the same manner as with Compound B had characteristics similar to those layers formed from Compound B.

EXAMPLE 4

Preparation of
1-[3-(2-acryloyloxyethoxy)-2-hydroxypropyl]-3[3-(2-acryloyloxyethoxy)-2-[[3-carboxyacryloyloxy]]-propyl]-5,5-dimethyl-2,4-imidizolidinedione

Compound D

Compound B (10.0 g, 0.025 m from Example 2) and 2.4 g maleic anhydride were charged into a 100 ml three-necked round bottom flask equipped with mechanical stirrer, reflux condenser, and $CaSO_4$ drying tube. The reaction was heated at 80° C. for six hours. At this time the reaction was terminated to yield a viscous slightly yellow liquid displaying a strong, broad infrared spectral absorbance centered at 3000 $cm^{-1}$, characteristic for carboxylic acids.

A layer of this material containing 2% of 2,2-dimethoxy-2-phenylacetophenone was prepared as in Example 1. This layer was cured to insolubility with a Hanovia 3D960 mercury arc lamp in 60 seconds. The sample was 6 cm from the light source.

EXAMPLES 5-10

Various amounts of Compounds A and B were mixed with trimethylolpropanetriacrylate (TMPTA) and 2% by weight of the photopolymerization initiator of Example 1 added. Each mixture was diluted with an equal weight of acetone and coated onto 12 µm polyester film and dried. The dried coating was 2.5 µm thick. On exposure in air at a distance of 6 cm the radiation from a 100 watt Hanovia 3D690 lamp and the time measured at which each become insoluble in acetone. The data obtained is recorded in Table I.

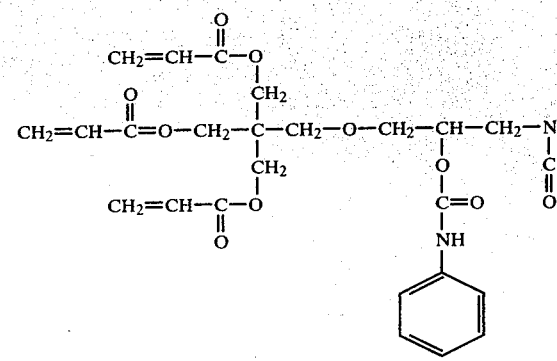

TABLE I

| Exp. No. | Composition Compound (%) | TMPTA | Cure Time (Sec.) |
|---|---|---|---|
| 4 | None | 100 | 600 |
| 5 | A (17) | 83 | 80 |
| 6 | A (28) | 72 | 60 |
| 7 | A (50) | 50 | 50 |
| 8 | A (100) | 0 | 10 |
| 9 | B (100) | 0 | 30 |

By reference to Table I it can be seen that TMPTA requires 10 minutes to reach insolubility and that with the addition of 17% of Compound A (from Example 1) the cure time is reduced to 80 seconds and with increasing amounts of A, the composition cures faster until at 100% A, the composition under the stated conditions cures in only 10 seconds. Comparable results can be obtained with Compound B.

EXAMPLE 11

A layer, 2.5 µm in thickness, of Compound B containing 2% of the photopolymerization catalyst of Example 1 on 12 µm polyester film was prepared as described in Example 1. A patterned template was placed over the layer and exposed in the UV Processor to one pass at 12 m/min. of an 80 watts/cm lamp. The exposed sheet was washed with cold water leaving an image having excellent resolution.

EXAMPLE 12

One part polyacrylic acid, one part compound A from Example 1, five parts water, five parts ethanol and 0.02 parts of the photopolymerization catalyst of Example 1 were mixed together to form a solution. A layer 5.0 m in thickness of this solution was coated onto 12 m polyester as described in Example 1. A patterned template was placed over the layer and exposed by a Hanovia 3D690 mercury arc lamp at a distance of 6 cm for two minutes. The exposed sheet was developed with cold water leaving an image having excellent resolution.

PREPARATION OF COMPOUND E

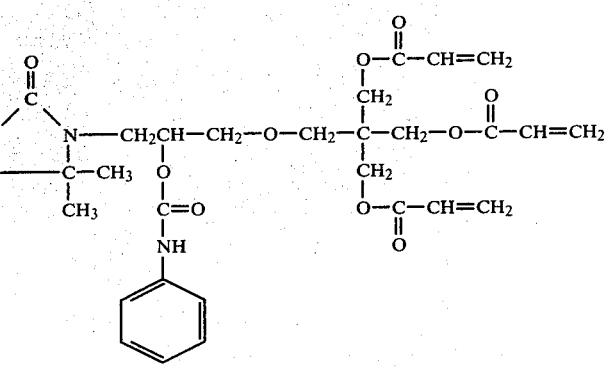

Compound A (20.4 g from Example 1) and 10.6 ml dry tetrahydrofuran were dissolved in a 250 ml 3-necked round bottom flask equipped with a magnetic stirrer, reflux condenser, pressure equalizing dropping funnel and CaSO₄ drying tube. 5.7 g phenylisocyanate was added dropwise over the course of five minutes. The reaction was terminated after stirring for twenty hours at room temperature. The lack of an isocyanate infrared absorption band indicates the reaction of the isocyanate to be quantitative.

A layer of this material containing 2% of the photopolymerization catalyst of Example 1 was prepared as in Example 1. This layer was cured to insolubility with a Hanovia 3D690 mercury arc lamp in 15 seconds. The sample was 6 cm from the light source.

Preparation of
1,3-Bis[3-(2-allyloxyethoxy)-2-hydroxypropyl]-5,5-dimethyl-2,4-imidizolidinedione

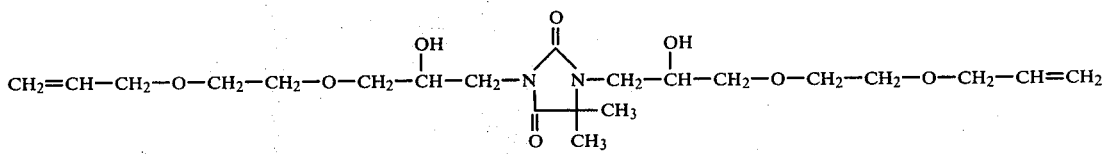

COMPOUND F 2-allyloxyethanol (20.43 g, 0.1 m), 0.03 g 4-methoxyphenol, and 0.30 g borontrifluoride etherate were charged into a 250 ml three-necked round bottom flask equipped with mechanical stirrer, pressure equalizing dropping funnel, reflux condenser and CaSO₄ drying tube. The reaction flask temperature was heated to 80°

C. and 13.8 g 1,3-bis(2,3-epoxypropyl)-5,5-dimethyl-2,4-imidizolidinedione in 4.5 g chloroform was added dropwise over 30 minutes. The reaction was maintained at 80° for 17 hours. At this time titration of residual epoxide groups indicated that the reaction was 99% complete. The chloroform was removed by vacuum distillation leaving as residue a colorless liquid.

EXAMPLE 15

Into a 250 ml three-necked round bottom flask equipped with mechanical stirrer, pressure equalizing dropping funnel, reflux condenser, and calcium sulfate drying tube were charged 103.0 g pentaerythritol triacrylate (hydroxy equivalent weight of 515), 23.2 g 2-hydroxyethyl acrylate (0.2 m), 0.08 g 4-methoxyphenol, and 1.0 g borontrifluoride etherate. The reaction flask was heated to 75° C. and 55.2 g (0.40 m epoxy equivalency) 1,3-bis(2,3-epoxypropyl)-5,5-dimethyl-2,4-imidizolidinedione in 20 ml chloroform was added dropwise over one hour. After the addition, the reaction flask temperature was raised to 88° C. and stirred for 18.0 hours. At this time, titration of an aliquote for unreacted epoxide indicated the reaction was greater than 99% complete. The volatiles were removed by vacuum distillation leaving a viscous liquid which contains a mixture of bis(triacryloyl)-, bis(monoacryloyl)-, and the unsymmetrical monoacryloyl-triacryloyl-imidizolidinedione, and impurities, introduced with the pentaerythritol triacrylate.

A layer of the reaction product of Example 15, prepared to contain 2% Irgacure 651 and cured as described in Example 1, had abrasion and chemical resistance characteristics similar to those of the layer of Example 1.

I claim:

1. A compound of the formula:

$$A^1-Z-A^2$$

wherein $A^1$ and $A^2$ are independently groups having terminal ethylenic unsaturation said groups having the formula:

$$R-O-CH_2-\underset{\underset{R^1}{|}}{\overset{\overset{OR^2}{|}}{C}}-R^3-$$

in which R—O— is a monovalent residue of an aliphatic terminally unsaturated primary alcohol, ROH, where R is selected from the formulae:

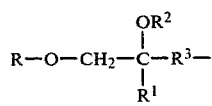

and $$[E-(CH_2)_b-]_m-R^5-(CH_2)_c$$

wherein

E is selected from the formulae

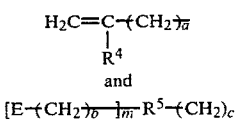

and

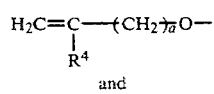

a and c are independently integers of from 1 to 6,
b is zero or an integer of from 1 to 6,
$R^1$ and $R^4$ are independently hydrogen or methyl,
$R^5$ is an aliphatic group having 1 to 15 carbon atoms which may be interrupted with up to two groups selected from the class consisting of ether oxygen groups or

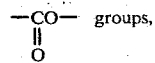 groups, $R^5$ having a valence of m+1 wherein m is an integer of 1 to 5,
$R^2$ is selected from the group of hydrogen,

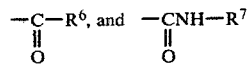

wherein
$R^6$ is selected from alkyl and alkenyl groups having up to 5 carbon atoms,
$R^7$ is an aliphatic group of up to 8 carbon atoms or aromatic group of up to 8 carbon atoms,
$R^3$ is an alkylene group having 1 to 6 carbon atoms and up to one catenary oxygen in the group, and
Z is a heterocyclic group of the formula:

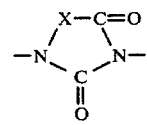

wherein X is a divalent group required to complete a 5-membered heterocyclic ring and is selected from the group of

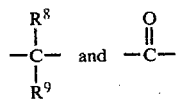

wherein $R^8$ and $R^9$ are independently selected from hydrogen, alkyl groups of 1 to 4 carbon atoms, cycloalkyl groups of 3 to 6 carbon atoms, and phenyl groups, and
$A^3$ is a group having terminal ethylenic unsaturation as defined above for $A^1$ and $A^2$.

2. The compound of claim 1 wherein $R^2$ is

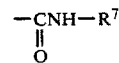

wherein $R^7$ is selected from alkyl group, phenyl group, acryloyloxyalkyl group, and methacryloyloxyalkyl group.

3. The compound of claim 1 wherein $R^2$ is

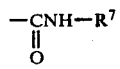

and R⁷ is selected from alkyl groups of up to eight carbon atoms and phenyl groups.

4. The compound of claim 1 wherein $R^2$ is hydrogen and $R^5$ is an alkyl group having a valence of 2 to 6 with up to two catenary ether oxygen atoms.

5. The compound of claim 4 wherein X is

6. The compound of claim 5 wherein $R^8$ and $R^9$ are independently selected from hydrogen and alkyl group of 1 to 4 carbon atoms, and $R^5$ is an alkyl group having a valence of 2 to 6 with up to two catenary ether oxygen atoms.

7. The compound of claim 5 wherein E is

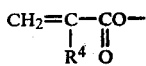

and m is 2 to 5.

8. The compound of claim 6 wherein E is

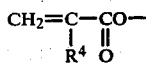

and m is 2 to 5.

9. The compound of claim 8 wherein X is

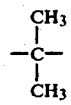

10. The compound of claim 7 wherein $R^2$ is selected from hydrogen,

wherein $R^6$ is selected from alkenyl or alkyl radicals of 2 to 5 carbon atoms and $R^7$ is selected from the group of alkyl radical of up to eight carbon atoms, phenyl radical, acryloyloxyalkyl radical and methacryloyloxyalkyl radical.

11. The compound of claim 8 wherein $R^2$ is selected from hydrogen,

wherein $R^6$ is selected from alkenyl or alkyl radicals of 2 to 5 carbon atoms and $R^7$ is selected from the group of alkyl radical of up to eight carbon atoms, phenyl radical, acryloyloxyalkyl radical or methacryloyloxyalkyl radical.

12. The compound of claim 9 wherein $R^2$ is selected from hydrogen,

wherein $R^6$ is selected from alkenyl or alkyl radicals of 2 to 5 carbon atoms and $R^7$ is selected from the group of alkyl radical of up to eight carbon atoms, phenyl radical, acryloyloxyalkyl radical or methacryloyloxyalkyl radical.

13. The compound of claim 1 wherein $R^5$ is an alkyl group having a valence of 2 to 6 with up to two catenary ether oxygen atoms.

14. The compound of claim 13 having no catenary oxygen atoms in $R^5$.

15. The compound of claim 1 wherein $R^2$ is selected from

and $R^6$ is selected from alkyl and alkenyl having 2 to 5 carbon atoms.

* * * * *